(12) United States Patent
Schwartz

(10) Patent No.: US 6,746,463 B1
(45) Date of Patent: Jun. 8, 2004

(54) DEVICE FOR PERCUTANEOUS CUTTING AND DILATING A STENOSIS OF THE AORTIC VALVE

(75) Inventor: Leonard Schwartz, Toronto (CA)

(73) Assignee: SciMed Life Systems, Inc, Maple Grove, MN (US)

( * ) Notice: Subject to any disclaimer, the term of this patent is extended or adjusted under 35 U.S.C. 154(b) by 0 days.

(21) Appl. No.: 10/353,827

(22) Filed: Jan. 27, 2003

(51) Int. Cl.[7] .................... A61B 17/20; A61D 1/02
(52) U.S. Cl. ............................ 606/159; 604/22
(58) Field of Search .................. 604/22, 104, 106, 604/509, 96.01; 606/159, 170, 191, 192, 198

(56) References Cited

U.S. PATENT DOCUMENTS

| | | |
|---|---|---|
| 4,886,061 A | 12/1989 | Fischell et al. |
| 5,009,659 A * | 4/1991 | Hamlin et al. ............ 606/159 |
| 5,176,693 A | 1/1993 | Pannek, Jr. |
| 5,192,291 A | 3/1993 | Pannek, Jr. |
| 5,336,234 A | 8/1994 | Vigil et al. |
| 5,556,408 A | 9/1996 | Farhat |
| 5,616,149 A * | 4/1997 | Barath ..................... 606/159 |
| 5,697,944 A * | 12/1997 | Lary ....................... 606/159 |
| 5,713,913 A | 2/1998 | Lary et al. |
| 5,792,158 A | 8/1998 | Lary |
| 5,797,935 A | 8/1998 | Barath |
| 6,096,054 A | 8/2000 | Wyzgala et al. |

\* cited by examiner

*Primary Examiner*—Loan H. Thanh
*Assistant Examiner*—Lina R Kontos
(74) *Attorney, Agent, or Firm*—Nydegger & Associates

(57) ABSTRACT

A device for incising a stenosis in the aortic valve of a patient includes an elongated balloon catheter, with at least one straight blade mounted on the balloon. Specifically, the blade is coplanar with the axis of the catheter, and the proximal end of the blade is located adjacent the proximal end of the balloon. In operation, the balloon/blade combination is advanced into the vasculature and positioned distal to the stenosis to be incised. The balloon is then inflated. With this inflation, the blade is inclined relative to the axis of the catheter with an increasing distance between the blade and the axis in a distal direction. The device is then retracted, proximally, to incise the stenosis.

19 Claims, 2 Drawing Sheets

DEVICE FOR PERCUTANEOUS CUTTING AND DILATING A STENOSIS OF THE AORTIC VALVE

FIELD OF THE INVENTION

The present invention pertains generally to interventional medical devices. More particularly, the present invention pertains to catheters that can be used to incise tissue in the vasculature of a patient. The present invention is particularly, but not exclusively, useful as a catheter for incising the aortic valve between the left ventricle of the heart and the aorta for the purpose of relieving the heart condition known as aortic valve stenosis (AS).

BACKGROUND OF THE INVENTION

In its normal operation, the left ventricle of the heart pumps oxygen-rich blood to arteries in the vasculature of the body through the aorta. As the heart pumps, the aortic valve, which is located between the ventricle and the aorta, opens and closes to control the direction of blood flow. Specifically, during a heartbeat, the valve is open to allow blood to flow from the ventricle into the aorta. Between heartbeats, however, the aortic valve closes to form a tight seal that prevents blood from leaking back into the ventricle. For any of several reasons (e.g. aging, or birth defects), it can happen that the aortic valve is somehow damaged and may become stenosed. When this happens, the aortic valve does not open to its normal extent and the flow of blood from the heart into the aorta is constricted. This leads to a heart condition that is commonly known as aortic valve stenosis (AS).

In a patient with AS, the aortic valve is stenosed and the heart is forced to pump blood through a narrowed opening through the aortic valve. Over time, this narrowing causes pressure to build up in the left ventricle of the heart. In order to compensate for this pressure overload, the muscles of the left ventricle enlarge (hypertrophy) so that the heart can pump with more force. It eventually happens, however, that the stenosis in the aortic valve increases to the point the heart can no longer maintain adequate blood flow through the stenosis. At this point, the patient experiences several characteristic symptoms of AS. In general, this occurs when the aortic valve, when open, has a valve opening area that is approximately one square centimeter (1 cm$^2$).

Heretofore, the treatment for AS has been accomplished either surgically by doing a valve replacement, or by performing a percutaneous balloon valvuloplasty. In the case of a valve replacement, an extensive surgical procedure is required wherein the aortic valve is replaced either by a mechanical or a porcine valve. On the other hand, being a percutaneous procedure, balloon valvuloplasty is somewhat less involved than a valve replacement procedure. Nevertheless, for many reasons including a high recurrence rate, and despite its initial acceptance, balloon valvuloplasty is now used infrequently and only palliatively or as a bridge to surgery.

In light of the above it is an object of the present invention to provide a percutaneous device and method for treating aortic valve stenosis that effectively makes controlled shallow incisions in the leaflets, of the aortic valve to thereby establish a more normal flow of blood from the left ventricle of the heart into the aorta. Another object of the present invention is to provide a cutting device that can be safely advanced through the vasculature of a patient, and subsequently withdrawn therefrom, while permitting surgical incisions at selected locations in the vasculature. Still another object of the present invention is to provide a cutting device and method for treating aortic valve stenosis that is simple to manufacture, easy to use, and comparatively cost effective.

SUMMARY OF THE INVENTION

In accordance with the present invention, a cutting device for treating aortic valve stenosis includes a catheter that has an elongated balloon mounted near its distal end. As intended for the present invention, the balloon can be reconfigured on the catheter between an inflated configuration and a deflated configuration. Structurally, the balloon defines an axis and, in its inflated configuration, it has three identifiable sections that are located between its distal end and its proximal end. These sections are: a substantially conical-shaped distal section having a taper with an increasing radius in the proximal direction; a substantially conical-shaped proximal section having a taper with a decreasing radius in the proximal direction; and a substantially cylindrical-shaped intermediate section that is located between the distal section and the proximal section.

At least one, but as many as three or possibly four, substantially straight, elongated blades are attached to the balloon. Importantly, these blades are oriented on the balloon so as to be coplanar with the axis of the balloon. Further, each blade is formed with a sharp edge, and each blade is attached to the balloon to project the sharp edge of the blade in a radial direction from the axis of the balloon. In more detail, the proximal portion of each blade is attached to the proximal section of the balloon, with the distal end of the blade adjacent the distal end of the balloon. The blades, however, are longer than the proximal section of the balloon. Therefore, the distal portion and the distal end of each blade is not attached to the balloon.

In the operation of the present invention, the balloon (in its deflated configuration) is advanced into the vasculature of the patient. Specifically, for the treatment of AS, the balloon is positioned inside the left ventricle of the heart. This then places the balloon distal to the aortic valve. In any event, once the balloon is in the left ventricle it is then inflated.

In its inflated configuration, the balloon inclines each blade relative to the axis of the balloon. Specifically, this inclination is characterized by an increasing distance between the blade and the axis of the balloon, in a distal direction along the axis. In cooperation with the balloon, each blade is inclined relative to the balloon's axis at an angle ($\alpha$) that is established by the taper of the balloon's proximal section, when the balloon is inflated. Preferably, this angle ($\alpha$) is in a range between approximately zero degrees, when the balloon is in its deflated configuration, and approximately forty-five degrees, when the balloon is in its inflated configuration. (0°–45°). An important consequence of this is that, when the balloon is in its inflated configuration, the sharp edges of the blades are presented for cutting (incising) the aortic valve. More specifically, the distal portions and distal ends of respective blades are projected radially outward from the axis through a distance that extends beyond the radius of the cylindrical-shaped intermediate section.

An incising action on the aortic valve is accomplished as the inflated balloon is retracted through the aortic valve in a proximal direction. After the inflated balloon has been retracted through the aortic valve, and the valve has been incised, the balloon is deflated. The deflated balloon is then withdrawn from the vasculature and the procedure is completed.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
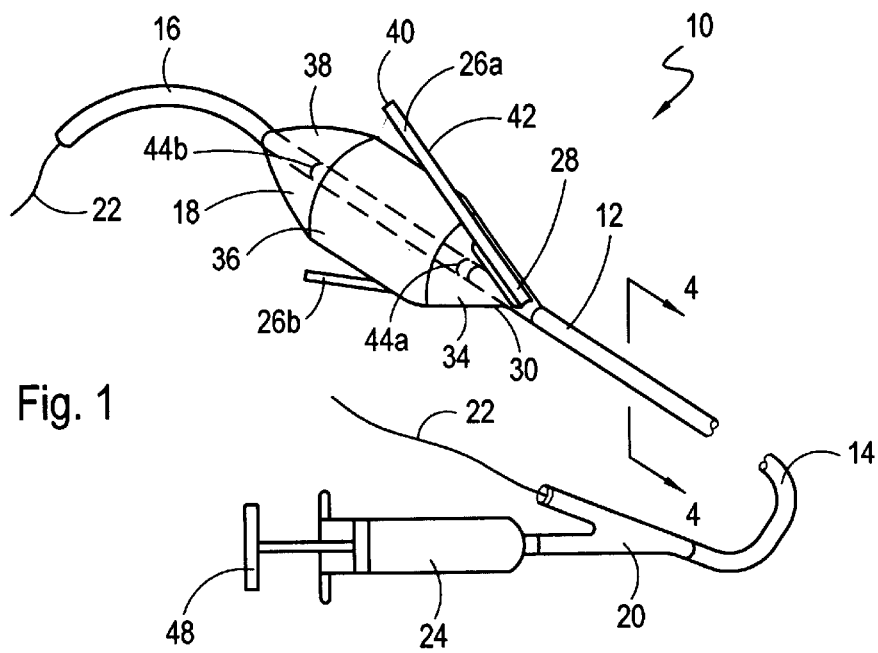
FIG. 1 is a perspective view of the incising device of the present invention.

Referring initially to FIG. 1, a system for incising tissue in accordance with the present invention is shown and generally designated 10. As shown, the system 10 includes a catheter 12 which has a distal end 14 and a proximal end 16. System 10 also has an inflatable, elongated balloon 18 that is mounted on the catheter 12 near its distal end 16. Further, it is seen that a y-site 20 is attached to the proximal end 14 of the catheter 12. Specifically, the y-site 20 allows the catheter 12 to be operationally engaged with a guidewire 22 for the purpose of advancing the catheter 12 over the guidewire 22 after the guidewire 22 has been pre-positioned in the vasculature of a patient (not shown). FIG. 1 also shows that an inflation/deflation device 24 can be connected to the y-site 20 for fluid communication with the balloon 18. Preferably, the balloon 18 is made of a resilient material such as Polyethylene Napthalate (PEN), or Polyethylene Teraphthlate.

Figure 2A:
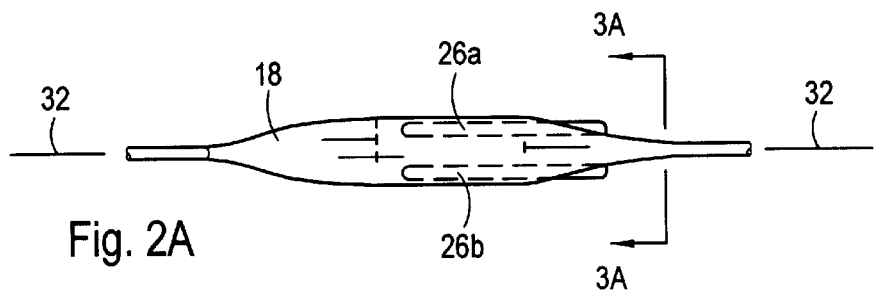
FIG. 2A is a side view of the balloon of the device of the present invention when the balloon is in its deflated configuration.

Still referring to FIG. 1, it will be seen that the system 10 of the present invention includes a plurality of substantially straight cutting blades 26, of which the cutting blades 26a and 26b are only exemplary. As envisioned for the present invention, the system 10 may include only one such blade 26, or it may include as many as three or four such blades 26. With this in mind, and using the blade 26a as a specific example for purposes of disclosure, it will be seen that the proximal end 28 of the blade 26a is positioned adjacent, or near, the proximal end 30 of the balloon 18. Further, it is to be appreciated that the blade 26a is oriented on the balloon 18 so that it is coplanar with the longitudinal axis 32 of the balloon 18 (see FIG. 2A). Also, it is to be appreciated by cross-referencing FIG. 1 with FIG. 2B, that the blade 26a is attached to a proximal section of the balloon 18. For purposes of the present invention, the blades 26 can be attached to the balloon 18 by any means well known in the pertinent art, such as by bonding.

Figure 2B:
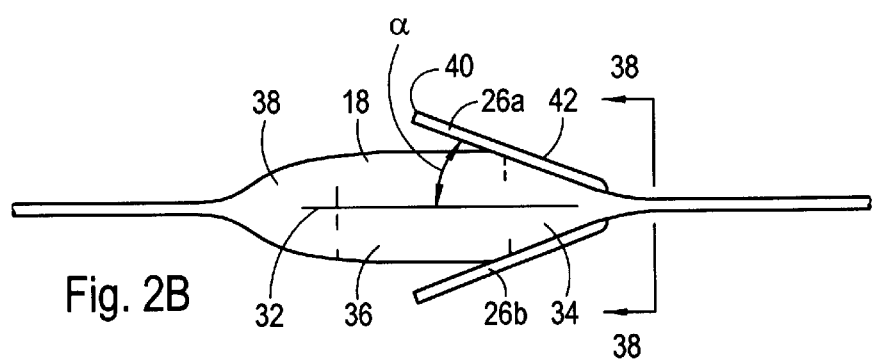
FIG. 2B is a side view of the balloon of the device of the present invention when the balloon is in its inflated configuration.

The structure for balloon 18 will be best understood by referencing both FIG. 1 and FIG. 2B. As shown, the balloon 18, when inflated, generally defines three sections. These are: a proximal section 34; an intermediate section 36; and a distal section 38. More specifically, when the balloon 18 is inflated, the proximal section 34 is generally conical-shaped and has a taper with an increasing radius in the distal direction. On the other hand, the intermediate section 36 is substantially cylindrical-shaped and has a generally constant radius. Again, there is a conical-shape for the distal section 38. This time, however, the taper for the distal section 38 has a decreasing radius in the distal direction. Preferably, the blade 26a is longer than the proximal section 34 and is attached to only the proximal section 34 of the balloon 18. Consequently, the distal end 40 of the blade 26a is not engaged with the balloon 18. As perhaps best seen in FIG. 2B, this cooperation of structure allows the sharp cutting edge 42 of the blade 26a, at the distal end 40 of the blade 26a, to extend radially outward from the axis 32 to a greater distance than the radius of the cylindrical-shaped intermediate section 36. Stated differently, with the balloon 18 in its inflated configuration, the blades 26 are inclined at an angle ($\alpha$) relative to the axis 32. Preferably, the angle ($\alpha$) is in a range between 0° and 45°.

FIG. 1 also shows that the system 10 of the present invention can include radiopaque markers 44a and 44b which will assist in positioning the balloon 18 in the vasculature of the patient. Identification of the balloon 18 at a location in the vasculature can be further facilitated by using a contrast medium to inflate the balloon 18. Other mechanisms, well known in the pertinent art, can be incorporated and used for these purposes.

Figure 3A:
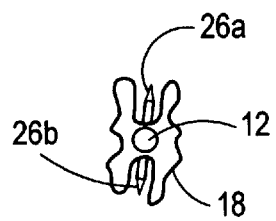
FIG. 3A is an end view of the balloon of the device of the present invention as seen along the line 3A—3A in FIG. 2A.
Figure 3B:
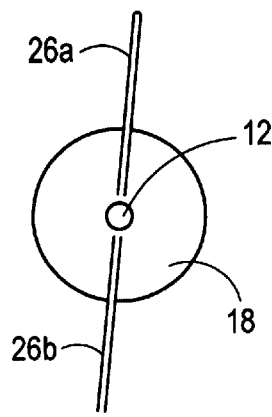
FIG. 3B is an end view of the balloon of the device of the present invention as seen along the line 3B—3B in FIG. 2B.
Figure 4:
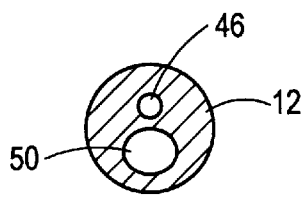
FIG. 4 is a cross sectional view of the catheter as seen along the line 4—4 in FIG. 1.

As envisioned for the present invention, the balloon 18 of the present invention can be reconfigured between a deflated configuration (FIG. 2A and FIG. 3A) and an inflated configuration (FIG. 2B and FIG. 3B). As implied above, the actual inflation and deflation of the balloon 18 is accomplished by manipulating the inflation device 24 (See FIG. 1). Specifically, for this purpose, the inflation/deflation device 24 is connected at the y-site 20 in fluid communication with an inflation lumen 46 (see FIG. 4). A manipulation of the plunger 48 (see FIG. 1) can then cause the balloon 18 to selectively inflate or deflate. FIG. 4 also shows that the catheter 12 is formed with a guidewire lumen 50 for receiving the guidewire 22 therethrough.

Figure 5:
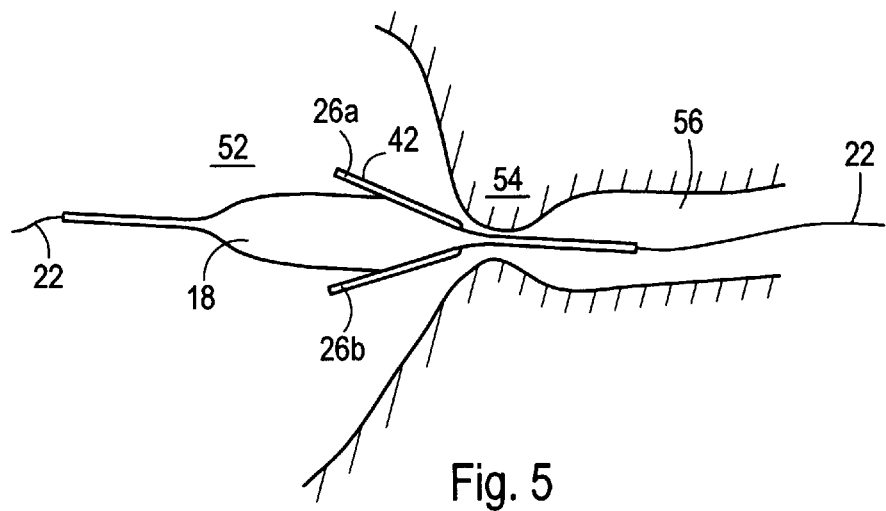
FIG. 5 is a schematic view of an inflated balloon of the present invention, positioned inside the left ventricle of a patent, ready for retraction in a proximal direction through an aortic valve for the purpose of incising the aortic valve.

Referring now to FIG. 5, in the operation of the system 10 of the present invention, the guidewire 22 is pre-positioned in the vasculature of the patient. The catheter 12, with the balloon 18 in its deflated configuration (FIG. 2A and FIG. 3A) is then advanced over the guidewire 22. Note that when the balloon 18 is in its deflated configuration, material of the balloon 18 will cover the blades 26 and thereby reduce the possibility of an unintended incision of tissue.

As intended for the operation of the present invention, the balloon 18 is advanced over the guidewire 22 until the balloon 18 has been positioned in the left ventricle 52 of the patient's heart. At this point, the inflation/deflation device 24 is manipulated to inflate the balloon 18 into its inflated configuration (FIG. 1, FIG. 2B and FIG. 3B). With the cutting blades 26 radially deployed, the system 10 is then retracted in a proximal direction through the aortic valve 54 and into the aorta 56. With this retraction, the cutting edges 42 of respective blades 26 incise the aortic valve 54 to relieve any stenosis that has developed in the aortic valve 54. After retraction, the balloon 18 is deflated, and the system 10 is withdrawn from the vasculature of the patient.

While the particular A Device for Percutaneous Cutting and Dilating a Stenosis of the Aortic Valve as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A cutting device which comprises:
   a catheter;
   an elongated balloon defining an axis, said balloon being mounted on said catheter for reconfiguration between an inflated configuration and a deflated configuration;
   a substantially straight, elongated blade formed with a sharp edge and having a proximal end portion and a distal end portion, with the proximal end portion attached to said balloon to orient said blade in a plane with the axis of said balloon and to project the sharp edge of the blade in a radial direction from the axis of said balloon; and
   a means for inflating the balloon into its inflated configuration to separate said distal end portion of said blade from said balloon and incline said blade relative to the axis, with an increasing distance between the blade and the axis in a distal direction, to present the sharp edge of said distal end portion of said blade for cutting an object as said device is moved relative to the object in a proximal direction.

2. A device as recited in claim 1 further comprising a guidewire for advancing said catheter through the vasculature of a patent to position said balloon for cutting tissue at a predetermined site in the vasculature.

3. A device as recited in claim 2 wherein the predetermined site in the vasculature is the valve between the left ventricle of the heart and the aorta.

4. A device as recited in claim 1 wherein said balloon has a distal end and a proximal end and, in its inflated configuration, said balloon further comprises:
   a substantially conical-shaped distal section having a taper with increasing radius in the proximal direction;
   a substantially conical-shaped proximal section having a taper with decreasing radius in the proximal direction; and
   a substantially cylindrical-shaped intermediate section located between said distal section and said proximal section.

5. A device as recited in claim 4 wherein said blade is attached to said proximal section of said balloon with the proximal end of said blade adjacent the proximal end of said balloon.

6. A device as recited in claim 5 wherein said proximal portion is attached to said balloon and said distal portion is formed with the sharp edge for cutting.

7. A device as recited in claim 6 wherein the incline of said blade relative to the axis is established by the taper of said proximal section of said balloon and is in a range between approximately zero degrees, when said balloon is in its deflated configuration, and approximately forty-five degrees, when said balloon is in its inflated configuration (0°–45°).

8. A device as recited in claim 1 further comprising a plurality of said blades.

9. A device as recited in claim 1 wherein said balloon covers said blade when said balloon is in its deflated configuration.

10. A device as recited in claim 1 wherein said balloon is inflated with a contrast medium.

11. A device for incising a stenosis which comprises:
    a substantially straight elongated blade having a proximal end portion and a distal end portion, with a sharp cutting edge in at least said distal end portion;
    a means for advancing the elongated blade in a distal direction along a predetermined path into the vasculature of a patient, to position the blade at a location distal to the stenosis;
    a means for inclining the blade relative to the path to separate said distal end portion of said blade from a balloon with an increasing distance between the blade and the path in the distal direction; and
    a means for retracting the blade in a proximal direction along the path to incise the stenosis with the cutting edge of the blade.

12. A device as recited in claim 11 wherein the advancing means is a catheter and the inclining means is a balloon.

13. A device as recited in claim 12 wherein the balloon has a distal end and a proximal end and, when inflated, the balloon further comprises;
    a substantially conical-shaped distal section having a taper with increasing radius in the proximal direction;
    a substantially conical-shaped proximal section having a taper with decreasing radius in the proximal direction; and
    a substantially cylindrical-shaped intermediate section located between the distal section and the proximal section.

14. A device as recited in claim 13 wherein the blade is attached to the proximal section of the balloon with the proximal end of the blade adjacent the proximal end of the balloon.

15. A device as recited in claim 14 wherein the blade has a distal portion and a proximal portion, wherein the proximal portion is attached to the balloon and the distal portion is formed with the sharp edge for cutting.

16. A device as recited in claim 15 wherein the incline of the blade relative to the path is established by the taper of the proximal section of the balloon and is in a range between approximately zero degrees, and approximately forty-five degrees (0°–45°).

17. A method for incising a stenosis which comprises the steps of:
    providing a substantially straight elongated blade having a proximal end portion and a distal end portion, with a sharp cutting edge in at least said distal end portion;
    advancing the elongated blade in a distal direction along a predetermined path into the vasculature of a patient, to position the blade distal to the stenosis;
    inclining the blade relative to the path to separate said distal end portion of said blade from a balloon with an increasing distance between the blade and the path in the distal direction; and
    retracting the blade in a proximal direction along the path to incise the stenosis with the cutting edge of the blade.

18. A method as recited in claim 17 wherein the inclining step is accomplished by inflating a balloon from a deflated configuration into an inflated configuration, and wherein the balloon, in its inflated configuration, has a distal end and a proximal end with a substantially conical-shaped distal section having a taper with increasing radius in the proximal direction, a substantially conical-shaped proximal section having a taper with decreasing radius in the proximal direction, and a substantially cylindrical-shaped intermediate section located between the distal section and the proximal section, and further wherein the blade is attached to the proximal section of the balloon with the proximal end of the blade adjacent the proximal end of the balloon to incline the blade relative to the path in a range between approximately zero degrees, when the balloon is in its deflated configuration, and approximately forty-five degrees, when the balloon is in its inflated configuration (0°–45°).

19. A method as recited in claim 17 further comprising the steps of:

deflating the balloon after the retracting step; and withdrawing the device from the vasculature of the patient after the deflating step.

\* \* \* \* \*